United States Patent [19]

Burk et al.

[11] Patent Number: 4,801,809
[45] Date of Patent: Jan. 31, 1989

[54] SHEET INSPECTION APPARATUS AND METHODS PROVIDING SIMULTANEOUS RESOLUTION OF MEASUREMENT ZONES AND WAVELENGTH BANDS

[75] Inventors: Gary N. Burk; Paul Williams, both of Columbus, Ohio

[73] Assignee: Process Automation Business, Inc., Columbus, Ohio

[21] Appl. No.: 72,505

[22] Filed: Jul. 13, 1987

[51] Int. Cl.⁴ ............................................. G01N 21/86
[52] U.S. Cl. .................................... 250/559; 250/563; 250/226
[58] Field of Search .............. 250/571, 572, 559, 562, 250/563, 226; 356/326, 328, 331–334, 429–431, 419, 435

[56] References Cited

U.S. PATENT DOCUMENTS

| | | | |
|---|---|---|---|
| 3,673,865 | 7/1972 | Michaelsen | 73/159 |
| 3,965,356 | 6/1976 | Howarth | 250/571 |
| 4,224,513 | 9/1980 | Casey et al. | 250/571 |
| 4,544,271 | 10/1985 | Yamamoto | 356/328 |
| 4,588,885 | 5/1986 | Lovoi et al. | 250/226 |
| 4,648,712 | 3/1987 | Brenholdt | 250/571 |
| 4,673,988 | 6/1987 | Jansson et al. | 358/280 |
| 4,674,871 | 6/1987 | Shifrin | 356/73 |
| 4,676,647 | 6/1987 | Kikkawa et al. | 356/382 |
| 4,710,642 | 12/1987 | McNeil | 250/571 |

*Primary Examiner*—David C. Nelms
*Attorney, Agent, or Firm*—Richard H. Berneike

[57] ABSTRACT

Disclosed are sheet inspection apparatus and methods for rapid, repetitive measurement of a quality attribute in each of a plurality of measurement zones of a continuously-manufactured sheet of material, wherein measurement is based on the interaction of one or more radiation wavelength bands with one or more constituents of the sheet. Simultaneous resolution of measurement zones is provided in both scanning and non-scanning applications.

32 Claims, 1 Drawing Sheet

SHEET INSPECTION APPARATUS AND METHODS PROVIDING SIMULTANEOUS RESOLUTION OF MEASUREMENT ZONES AND WAVELENGTH BANDS

BACKGROUND OF THE INVENTION

1. Technical Field

The present invention relates to sheet inspection systems of the type used in measuring quality attributes of a moving sheet of material during its continuous manufacture. More particularly, the invention pertains to those systems which derive such measurements from prior measurements of physical properties of the sheet, which prior measurements are based on the interaction of one or more selected wavelength bands of radiant energy with one or more constituents of the sheet. Yet more particularly, the invention concerns those systems which must repeatedly produce such measurements for each of a plurality of measurement zones (also known as "data boxes").

2. Description of the Background Art

Systems of the above description have been in use for many years. In a typical arrangement, one or more sensors mounted on a conventional sheet-traversing structure move back and forth across the entire cross-machine width of the sheet in order to provide for measurement in each measurement zone. This reciprocating motion is commonly referred to as "scanning", The sensors typically employ a source of radiant energy. Radiation directed from the source and interacting with the sheet is detected by a detection system which typically produces analog signals indicative of one or more physical properties of the sheet. Examples of such physical properties are transmittance, reflectance, and flourescence. The physical property is in turn indicative of one or more quality attributes. Examples of such quality attributes are basis weight, moisture content, color, degree of cure, thickness, gloss, and ash content.

For some quality attributes, it is unnecessary to design the sensor to detect radiation at two or more selected ranges of wavelength (hereinafter "wavelength bands"). In measuring gloss, for example, a source of visible light is used with a suitable source/detector geometry, and a measurement of gloss is produced from the reflectance of a relatively broad range of visible light wavelengths without regard to the reflectance of narrower bands within the visible range. However, the ability to measure other quality attributes such as color, moisture content, polymer content and weight per unit area may be based upon independent detection of a plurality of selected wavelength bands with one or more constituents of the sheet. In measuring color, for example, it is necessary to resolve light which has interacted with the sheet into a plurality (typically, at least sixteen) of wavelength bands and to measure the physical property for each of the bands before the physical property measurements are combined to produce a single measurement of color.

As mentioned above, the sensor typically moves in reciprocating fashion across the entire cross-machine width of the sheet. The time required for the sensor to traverse the entire width may be on the order of fifteen to sixty seconds. In comparison, the sheet may be moving in the machine direction at speeds in excess of 3,000 feet per minute. Consequently, between successive appearances of a sensor in a particular measurement zone, several hundreds of feet of production may have passed the sensor without measurement in that zone. Moreover, in the time it takes the sensor to travel from one zone to the next, over 50 feet of production may have passed given the above speeds. Thus, the line of measurement for a particular scan may be viewed as a very long diagonal extending from one edge of the sheet to the other.

One of the technical problems thus presented is that when changes in a quality attributes are observed, it is difficult to know the extent to which the changes result from MD (machine direction) variation of the attribute as opposed to CD (cross-machine direction) variation. This poses a problem in controlling the quality attribute in that the steps taken to correct for MD variation differ markedly from those taken to correct for CD variation. Thus, in order to immediately implement the right combination of control steps, the precise nature of the variation must be known. Since the motion of the sensors precludes knowledge of the nature of the variation at any particular time, current control schemes employ assumptions respecting the directional nature of the variation in order to calculate optimal combinations of control steps. These calculations are repeatedly updated to reflect the most recent measurement data for the quality attribute of interest.

In addition to the foregoing problem, there are various maintenance and precision problems associated with the mechanical motion necessitated by conventional scanning sensors.

Accordingly, in the field of measurement and control of continuously-produced sheet materials wherein measurement is based on the interaction of one or more selected radiation wavelength bands with the sheet, and particularly in the area of papermaking, there has been a continuing need for sensors which can provide more rapid measurement of quality attributes in each measurement zone of the sheet, and for sensors which can do so without resort to the conventional scanning motion.

It is an object of this invention to provide a non-scanning sensor for use in measuring, in each measurement zone of a moving sheet of material, a selected quality attribute of the sheet.

It is another object of this invention to provide a nonscanning sensor that is suitable for applications wherein measurement is based on the interaction of one or more radiation wavelength bands with one or more constituents of the sheet. It is a further object of this invention to provide such a sensor that is operable with a single detector unit so that conventional approaches employing plural detectors or time-multiplexing of radiation transmissions are unnecessary.

Yet another object of this invention is to provide, in systems which use scanning sensors, significant improvement in the ability to separate observed variations in a quality attribute into MD and CD components.

SUMMARY OF THE INVENTION

The present invention provides apparatus and associated methods of measuring a quality attribute of a moving sheet of material in each of a plurality of measurement zones extending across the sheet, wherein measurement is based on the interaction of one or more radiation wavelength bands with one or more constituents of the sheet. The invention is directed primarily to paper products, but also applies to other continuouslymanufactured materials such as plastic film and foil, for example.

In one aspect, the invention provides non-scanning apparatus and associated methods which disperse radiation that is directed from a source onto an imaged strip which extends across the entire cross-machine width of the sheet. The radiation, having interacted with the sheet, is dispersed into a spectrum including a plurality of radiation wavelength bands including at least one selected band for which measurements of the physical property are to be made before a measurement of the quality attribute is produced. A detector having a two-dimensional array of detection zones is positioned to resolve the spectrum into at least the selected wavelength bands, and to resolve the imaged strip into the required number of data boxes or measurement zones so that detector responses corresponding to the selected radiation wavelength bands may be produced for each measurement zone. Since the imaged portion extends across the entire crossmachine width of the sheet, no scanning motion is necessary.

In another aspect the invention provides, in sheet inspection apparatus employing a scanning motion, significant improvement in the ability to separate MD from CD components of variation in the quality attribute. This improvement derives from the fact that several measurement zones are simultaneously imaged, thus enabling substantially simultaneous measurement of the physical property for each of the selected wavelength bands in several measurement zones. This in turn permits the production of numerous "difference signals" proportional to the CD change in the physical property on which measurement of the quality attribute is based.

DESCRIPTION OF THE PREFERRED EMBODIMENT

The disclosure of the following documents is incorporated herein by reference: pending U.S. patent application Ser. No. 940,139, now abandoned, and U.S. Pat. No. 3,673,865 Michaelson.

Figure 1:
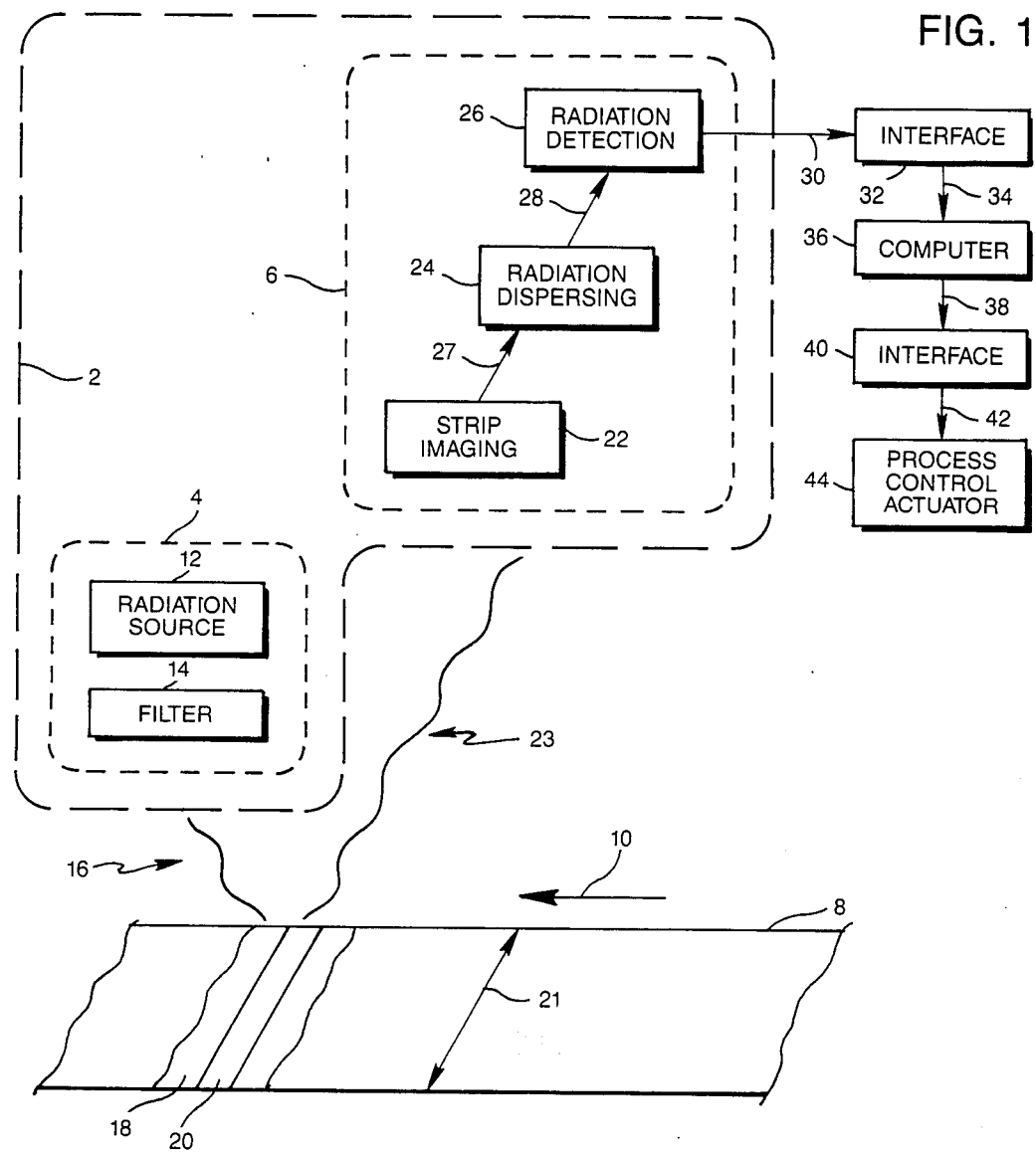
FIG. 1 is a schematic diagram of the preferred embodiment, illustrating a measurement and control system including a non-scanning sensor that employs a reflection geometry to measure reflectance across the entire crossmachine width of a moving sheet of paper for each of a plurality of selected wavelength bands.

Referring to FIG. 1 of the drawings, a sensor 2 is indicated by a dashed line enclosing a source unit 4 and an imaging and detection unit 6. The sensor 2 is of a class used for measuring a quality attribute of a continuouslymanufactured sheet 8 of material during manufacture thereof. The sheet 8 may be viewed as moving in the machine direction, indicated by the numeral 10.

The source unit 4 is indicated by a dashed line enclosing a source 12 of electromagnetic radiation and radiation filtering means 14. Depending on such factors as the spectral band emitted by the source 12 and the quality attribute for which measurements are to be made, the filtering means 14 may or may not be present in a particular application. When present, and except for applications in which the physical property of interest is flourescence, it may be placed at any suitable point in the radiation path between source and detector, though indicated in FIG. 1 as contained in the source unit 4. The source 12 may be a single source or a number of sources arranged side-by-side, depending on the requirements imposed by the width of the sheet 8 in relation to the applicable dimension of a single source. Alternatively, the source 12 may be a laser that in combination with a cylindrical lens can irradiate the entire cross-machine width 21 of the sheet 8. The particular source 12 of radiation may depend on the intensity and spectral band required for the application. For example, if the quality attribute to be measured is color, a relatively flat, highintensity source (i.e. one having a relatively uniform distribution of wavelengths) of visible light such as a xenon flash tube is preferable. Where the quality attribute is moisture content and measurement is based on the phenomenon of molecular resonance absorption, the source 12 may be a conventional tungsten lamp that emits infrared. Considerations attaching to the selection of a proper source are known in the art and need no further discussion.

Radiation, indicated by the numeral 16, is shown to be directed from the source 12 onto the sheet 8. The sheet 8 is thus irradiated over a portion 18 which includes a strip 20 extending across the entire crossmachine width 21 of the sheet. Some of the radiation 16 is reflected from the strip 20 (as indicated at 23) toward the imaging and detection unit 6. The imaging and detection unit 6 is indicated by a dashed line enclosing strip imaging means 22, radiation dispersing means 24, and radiation detecting means 26.

The strip imaging means 22 may be any suitable device or combination for forming an image of the strip 20 on the radiation dispersing means 24 as, for example, a projection slit and/or lens arrangement.

The radiation dispersing means 24 is preferably a diffraction grating having a dispersion and blaze angle that fit the requirements for the particular application. Less desirable dispersing means including prisms may be used to provide substantially the same result achieved by the diffraction grating. The diffraction grating is positioned with respect to the strip imaging means 22 so that the image of the strip 20 is formed thereon as required and is parallel to the grating rulings. The wavelength dispersion angle is thus orthogonal to the image of the strip. The dispersing means 24 disperses, into a spectrum including the plurality of selected wavelength bands, the radiation 27 that has interacted with the sheet 8 at the strip 20 and has followed a path corresponding to the strip imaging means 22, to provide dispersed radiation 28. The radiation detecting means 26 is preferably a single area detector providing two-dimensional resolution such as a CCD, CID, or vidicon. The detecting means 26 is positioned with respect to the dispersing means 24 so that a dispersed image of the strip 20 is formed on the detecting means. The dispersed radiation 28 impinges the detecting means 26 to produce detector responses 30 indicative of the reflectance of the sheet 8 in each measurement zone for each of the wavelength bands.

The number of selected wavelength bands, as well as their bandwidths, will depend on the quality attribute being measured, and may in some applications be affected by the presence of contaminants or other constituents of the sheet 8. (In connection with the latter, see, e.g., U.S. Pat. No. 4,577,104 Sturm.). For example, a satisfactory measurement of color requires a resolution of at least sixteen wavelength bands extending over the visible region. In comparison, a measurement of moisture content may require a resolution of as few as two wavelength bands, and a measurement of thickness may require only one.

Figure 2:
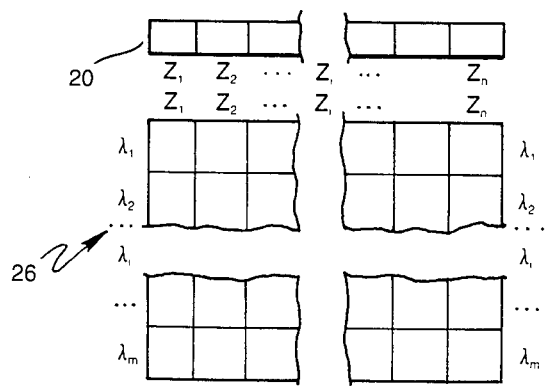
FIG. 2 is a schematic illustration of the measurement zones and detection zones associated with the imaged strip and area detector, respectively, of FIG. 1.

Referring to FIG. 2, the strip 20 is shown as including a number, "n", of measurement zones, "z", As is well known, this number is limited according to considerations including data acquisition speed and data processing speed, and will not be the same in every application. The detecting means 26 is schematically represented as including "m times n" detection zones corresponding both numerically and sequentially to the number, "m", of wavelength bands, "λ", into which it resolves the dispersed radiation 28, and the number of measurement zones, respectively. As is evident from the above, the strip imaging means 22 and the radiation dispersing means 24 function to effect a mapping of the dispersed image of the strip 20 onto the detecting means 26 to produce a one-to-one correspondence between a particular detection zone, and a particular wavelength band within a particular measurement zone. To this end, one or more lens arrangements (not shown) may be employed if necessary.

Thus, radiation is simultaneously detected in all detection zones, and from the radiation 28 impinging the detection zones there is produced for every measurement zone, "z", a plurality, "m times k", of detector responses 30, where "k" is the number of pixels in any given detection zone, "$z_i, \lambda_j$", Each of the detector responses 30 is indicative of the intensity of radiation impinging the associated pixel. In the embodiment of FIG. 1, the detector responses 30 are thus indicative of the reflectance of the sheet 8 at various wavelengths in various measurement zones. By known signal processing methods, the "k" detector responses 30 corresponding to any given detection zone "$z_i, \lambda_j$", can be summed to produce overall measurements of reflectance for the particular wavelength band and the particular measurement zone corresponding to that detection zone. Appropriate software may be employed to use only those detector responses 30 from detection zones corresponding to a selected wavelength band or to a plurality of selected wavelength bands. Moreover, by employing a high-speed data acquisition device such as a CCD for the radiation detecting means 26, and a high-speed data processing circuit such as that described in pending application Ser. No. 940,139, a complete group, "n times m times k", of detector responses 30 can be obtained, and thus a complete set, "n times m", of reflectance measurements can be made in a time interval on the order of fifteen milliseconds. This dramatically increases the ability to distinguish MD from CD variation in the quality attribute.

The detector responses 30 are communicated to an interface 32, (which may be similar to apparatus described in the above-cited pending application), converted to digital responses 34 and then communicated to a digital computer 36 in which calibration data relating to the physical property are stored. From the calibration data, the digital responses 34, and known formulae the computer 36 produces the measurements of the quality attribute. Typically, these are compared to targets entered into the computer 36, and appropriate digital control data 38 are converted through another interface 40 to control signals 42 which are communicated to a process control actuator 44.

The process control actuator 44 may comprise a set of valves for varying the flow rates of dyes or other coloring agents where the quality attribute is color, or it may comprise a set of heating elements or water spray nozzles where the quality attribute is moisture content, for example. Thus, the process control actuator 44 serves to effect a change in the quality attribute in response to measurements thereof.

In the preferred embodiment of FIG. 1, the strip 20 extends across the entire cross-machine width of the sheet 8 and there is therefore no need for the sensor 2 to be mounted on a sheet-traversing structure. Accordingly, the sensor 2 is located at a generally central position respecting the path of travel of the sheet 8, and is mounted on a suitable stationary structure (not shown). As indicated in the drawing, it will typically be necessary to locate the imaging and detection unit 6 considerably further from the sheet 8 than the source unit 4 in order to image a strip that extends across the entire width of the sheet. In an application where it is impractical to image the entire width of the sheet 8, the invention may be used in a scanning arrangement. In that case, the imaged strip 20 extends over as much of the sheet width as is expedient and, so long as the image covers a plurality of measurement zones, the invention can be used to significantly improve, with a single sensor, the ability to distinguish CD from MD variation in the quality attribute. This results from the ability to use several "difference signals" proportional to the CD change in the physical property (e.g. transmittance) on which measurement of the quality attribute is based. See, e.g., U.S. Pat. No. 3,673,865 Michaelsen wherein a limited version of that principle is applied in a scanning arrangement using two sensors.

In a modified version of the invention, the radiation dispersing means 24 is eliminated and a conventional filter wheel is provided in the source unit 4 or the detector unit 6. In that case the strip imaging means 24 (in combination with a suitable lens if necessary) forms an image of the strip directly onto the detecting means 26. Because of the speed disadvantages associated with this multiplexing arrangement, it is a less preferable alternative.

Although a reflection geometry is illustrated in FIG. 1, it is to be understood that the invention may be employed in other conventional geometries as well and, in general, the foregoing description of the preferred embodiment is intended as illustrative only. Thus, the description is not meant to restrict the scope of the invention beyond that defined by the following claims and their equivalents.

What is claimed is:

1. A non-scanning apparatus for use in measuring a quality attribute of a continuouslymanufactured sheet of paper in each of a plurality of measurement zones, comprising:

(a) a source of electromagnetic radiation for directing radiation onto a portion of said sheet, said portion including a strip extending across said plurality of measurement zones;

(b) means for filtering said radiation to pass a number of selected radiation wavelength bands;

(c) means for detecting radiation of said wavelength bands, said detecting means having an array of detection zones corresponding both numerically and sequentially to said measurement zones, so that for each of said radiation wavelength bands there is produced a plurality of detector responses associated with said plurality of measurement zones, said responses being indicative of the intensity of radiation impinging said detection zones and being dependent upon a physical property of the sheet such as transmittance or reflectance; and (d) means for imaging said strip to form an image thereof on said detecting means so that radiation which emits from said irradiating means, passes through said filtering means, and interacts with said sheet at said strip impinges said detection zones in accordance with said array correspondence.

2. A non-scanning apparatus as in claim 1 further comprising means for pre-processing said responses to produce output signals indicating standardized values for said physical property.

3. A non-scanning apparatus as in claim 2 wherein said strip extends across the entire cross-machine width of said sheet.

4. A non-scanning apparatus as in claim 3 wherein said quality attribute is moisture content.

5. A non-scanning apparatus as in claim 2 wherein said preprocessing means comprises an A/D converter which produces said output signals in response to said detector responses and high and low reference data associated with said detector responses.

6. A non-scanning apparatus as in claim 5 wherein said strip extends across the entire cross-machine width of said sheet.

7. A non-scanning apparatus as in claim 5 wherein said source and said detecting means are positioned with respect to each other and to said sheet so that said physical property is reflectance.

8. Apparatus for use in measuring a quality attribute of a continuously-manufactured sheet of material, wherein measurements of said quality attribute are derived from measurements of a physical property of said sheet, comprising:

(a) means for irradiating a portion of said sheet, said portion including a strip extending in a crossmachine direction across a plurality of measurement zones;

(b) means for detecting radiation that has emitted from said irradiating means, has interacted with said sheet at said strip, and has been dispersed into a plurality of wavelength bands, said detecting means having a plurality of detection zones arranged in a twodimensional array corresponding, in one dimension, to said plurality of measurement zones and, in the second dimension, to said plurality of wavelength bands, and being capable of producing for each of said detection zones a plurality of radiationintensity-dependent detector responses from which a measurement of said physical property can be derived; and (c) means for mapping a dispersed image of said strip onto said detecting means so that said dispersed radiation impinges said detection zones simultaneously said in accordance with said twodimensional array correspondence.

9. Apparatus as in claim 8 wherein said irradiating means and said detecting means are positioned with respect to each other and to said sheet so that said physical property is transmittance.

10. Apparatus as in claim 8 wherein said irradiating means and said detecting means are positioned with respect to each other and to said sheet so that said physical property is reflectance.

11. Apparatus as in claim 9 or 10 further comprising means for processing selected ones of said detector responses to produce a measurement of said quality attribute.

12. Apparatus as in claim 11 wherein said strip extends across the entire cross-machine width of said sheet and said apparatus is stationary.

13. Apparatus is in claim 12 wherein said irradiating means comprises a xenon flash tube.

14. Apparatus as in claim 11 further comprising means for pre-processing said detector responses to produce output signals indicating standardized values for said physical property.

15. Apparatus as in claim 14 wherein said preprocessing means comprises an A/D converter which produces said output signals in response to said detector responses and high and low reference data associated with said detector responses.

16. Apparatus as in claim 15 wherein said strip extends across the entire cross-machine width of said sheet.

17. Apparatus for use in measuring a quality attribute of a continuously-manufactured sheet of paper, wherein measurements of said quality are derived from measurements of a physical property of said sheet, comprising:

(a) means for irradiating a portion of said sheet, said portion including a strip extending across a plurality of measurement zones;

(b) means for imaging said strip (c) means for dispersing radiation interacting with said sheet at said strip into a spectrum including a plurality of wavelength bands in which said physical property is to be measured, said dispersing means being positioned with respect to said imaging means so that an image of said strip is formed thereon;

(d) a detector for detecting radiation dispersed by said dispersing means, said detector having a twodimensional array of detection zones corresponding numerically and sequentially in one dimension to said plurality of measurement zones, and in the second dimension to said plurality of wavelength bands, and being positioned with respect to said dispersing means so that said dispersed radiation is resolved in accordance with said array correspondence.

18. An apparatus as in claim 17 wherein said detector simultaneously detects radiation impinging said array of detection zones to produce, for each of said measurement zones, a plurality of detector responses indicative of the intensity of radiation in each of said plurality of wavelength bands.

19. An apparatus as in claim 18 further comprising means for pre-processing said detector responses to produce output signals indicating standardized values for said physical property.

20. An apparatus as in claim 19 wherein said preprocessing means comprises an A/D converter that produces, for each detector response, an output signal having a magnitude that depends on three data, one of which is said detector response, and the other two of which are high and low reference data associated with said detector response.

21. An apparatus as in claim 20 wherein said irradiating means comprises a xenon flash tube.

22. An apparatus as in claim 20 wherein said detector comprises a CCD array.

23. An apparatus as in claim 18 wherein said strip extends across the entire cross-machine width of said sheet of paper.

24. An apparatus as in claim 20 wherein said strip extends across the entire cross-machine width of said sheet of paper.

25. An apparatus as in claim 20 further comprising signal processing means, in communication with said preprocessing means, for processing said output signals to produce measurements of said quality attribute.

26. A method for measuring a quality attribute of a continuously-manufactured sheet of material in non-scanning fashion during manufacture thereof, comprising the steps of:
   (a) irradiating a portion of said sheet, said portion including a strip extending across a plurality of measurement zones;
   (b) forming an image of said strip on radiation dispersing means so that radiation interacting with said sheet at said strip impinges said dispersing means;
   (c) dispersing said radiation that impinges said dispersing means into a spectrum including a plurality of radiation wavelength bands, the reflectances or transmittances of which are measured prior to producing a measurement of said quality attribute for each of said measurement zones;
   (d) detecting said radiation corresponding to said wavelength bands in a manner such that the dispersed radiation is resolved in two dimensions, one dimension corresponding to said plurality of measurement zones and the other dimension corresponding to said plurality of wavelength bands to produce, for each wavelength band, a plurality of detector responses corresponding to said plurality of measurement zones; and
   (e) processing said detector responses to produce said measurement of said quality attribute for each measurement zone.

27. A method as in claim 26 further comprising the step of effecting a change in said quality attribute in response to said measurement.

28. A method as in claim 26 wherein said detecting step is performed simultaneously for all measurement zones.

29. A method as in claim 28 wherein said quality attribute is color.

30. A method as in claim 28 wherein said quality attribute is moisture content.

31. A method as in claim 28 wherein said quality attribute is weight per unit area.

32. A method as in claim 28 wherein said strip extends across the entire cross-machine width of said sheet.

* * * * *